US012597498B2

(12) United States Patent
Asano et al.

(10) Patent No.: US 12,597,498 B2
(45) Date of Patent: Apr. 7, 2026

(54) MEDICATION USE SUPPORT SYSTEM

(71) Applicant: DAIWA CAN COMPANY, Tokyo (JP)

(72) Inventors: Toshihiro Asano, Sagamihara (JP);
Keisuke Hashimoto, Sagamihara (JP);
Taichi Ijuin, Sagamihara (JP)

(73) Assignee: DAIWA CAN COMPANY, Tokyo (JP)

( * ) Notice: Subject to any disclaimer, the term of this
patent is extended or adjusted under 35
U.S.C. 154(b) by 0 days.

(21) Appl. No.: 19/022,882

(22) Filed: Jan. 15, 2025

(65) Prior Publication Data

US 2025/0157610 A1 May 15, 2025

Related U.S. Application Data

(63) Continuation of application No.
PCT/JP2023/026125, filed on Jul. 14, 2023.

(30) Foreign Application Priority Data

Jul. 15, 2022 (JP) ................................ 2022-114191

(51) Int. Cl.
*G16H 20/10* (2018.01)
*G16H 40/63* (2018.01)
*G16H 70/40* (2018.01)

(52) U.S. Cl.
CPC ............. *G16H 20/10* (2018.01); *G16H 40/63*
(2018.01); *G16H 70/40* (2018.01)

(58) Field of Classification Search
CPC ........ G16H 10/20; G16H 10/40; G16H 10/60;
G16H 10/65; G16H 15/00; G16H 20/10;
(Continued)

(56) References Cited

U.S. PATENT DOCUMENTS

2006/0187055 A1* 8/2006 Colby .............. G06K 19/07749
343/841
2006/0187060 A1* 8/2006 Colby .................... H01Q 1/526
343/841
(Continued)

FOREIGN PATENT DOCUMENTS

JP 2003-16185 A 1/2003
JP 2017021645 A * 1/2017
(Continued)

OTHER PUBLICATIONS

International Search Report, including English language translation,
Aug. 22, 2023, for PCT/JP2023/026125.

*Primary Examiner* — Chad A Newton
(74) *Attorney, Agent, or Firm* — John P. White

(57) ABSTRACT

A medication use support system including a communica-
tion device provided to a medicine and a terminal that stores
and manages medication information, wherein the terminal
includes: a reading unit which reads first trigger information
for acquiring information of the medicine; a communication
unit which performs wireless communication with the com-
munication device; a storage unit which stores management
information of the medicine; a display unit which displays a
medication use management screen including the manage-
ment information of the medicine; and a control unit which
determines a use status of the medicine by communication
with the communication device, the communication device
is in a communicable state with the terminal when not
shielded by the electromagnetic wave shielding member and
transmits second trigger information to the communication
unit in the communicable state.

12 Claims, 7 Drawing Sheets

(58) Field of Classification Search
CPC ........ G16H 20/13; G16H 20/17; G16H 20/30;
G16H 20/40; G16H 20/60; G16H 20/70;
G16H 20/90; G16H 30/20; G16H 30/40;
G16H 40/20; G16H 40/40; G16H 40/60;
G16H 40/63; G16H 40/67; G16H 50/20;
G16H 50/30; G16H 50/50; G16H 50/70;
G16H 50/80; G16H 70/20; G16H 70/40;
G16H 70/60; G16H 80/00
See application file for complete search history.

(56)                References Cited

U.S. PATENT DOCUMENTS

2006/0187061  A1 *   8/2006  Colby ...................... H01Q 1/22
                                           343/841
2016/0310663  A1 *  10/2016  Dantsker ........... A61M 5/31571

FOREIGN PATENT DOCUMENTS

JP           2019013518  A  *   1/2019
JP           2021018666  A  *   2/2021
WO      WO-2006107397  A2 *  10/2006   ....... G06K 19/07327

* cited by examiner

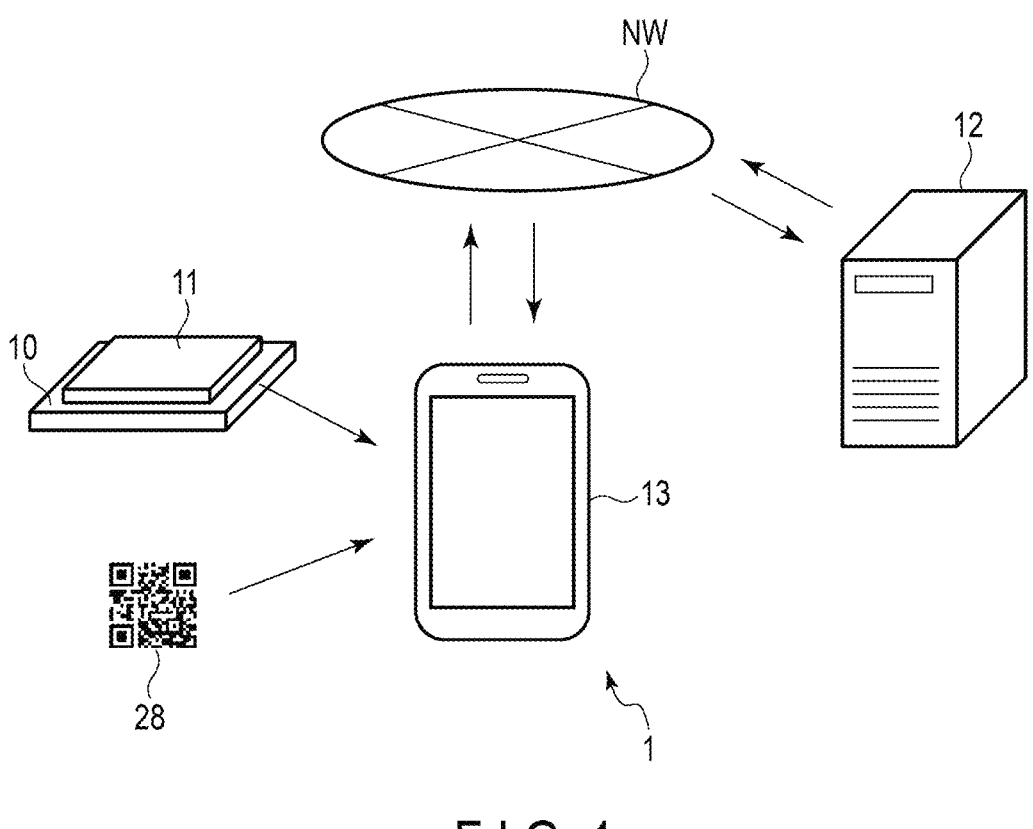
F I G. 1

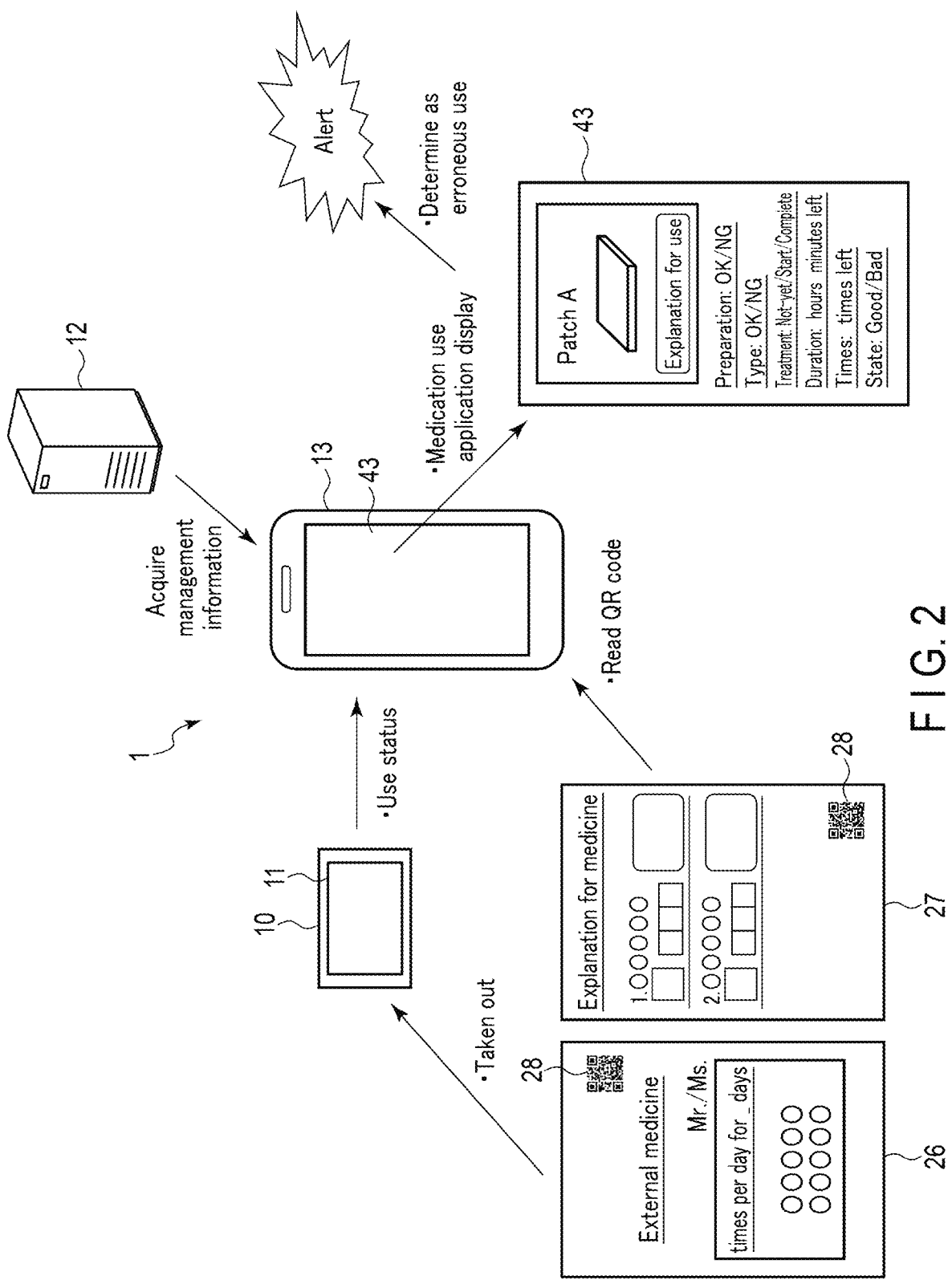
F I G. 2

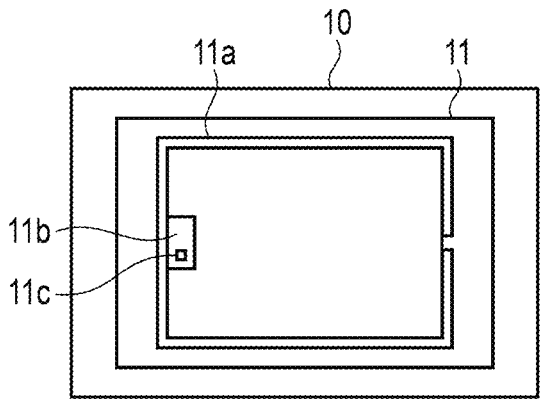
F I G. 3
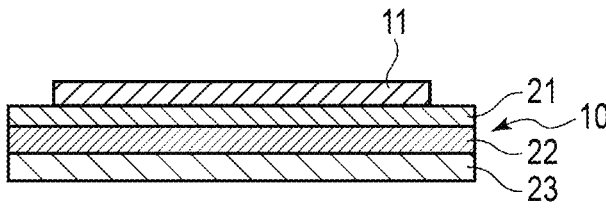
F I G. 4

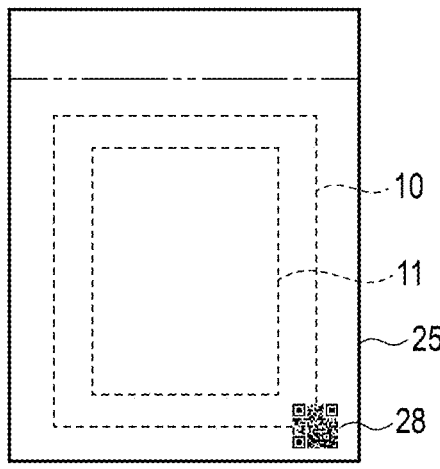
F I G. 5
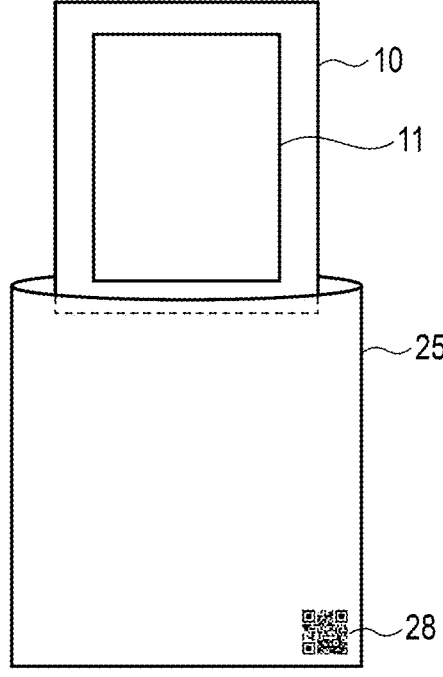
F I G. 6

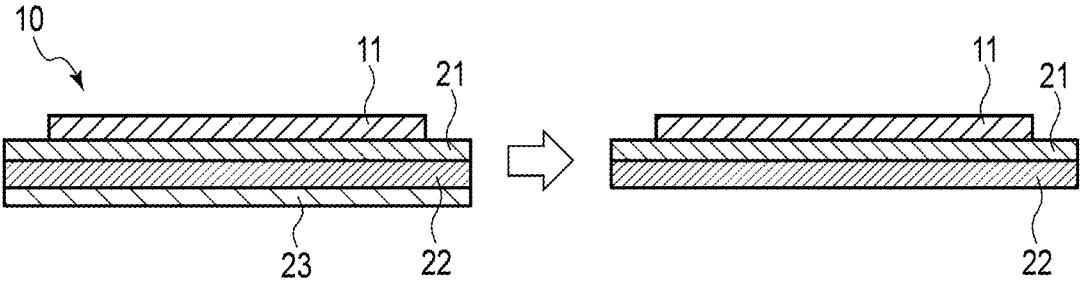
F I G. 7
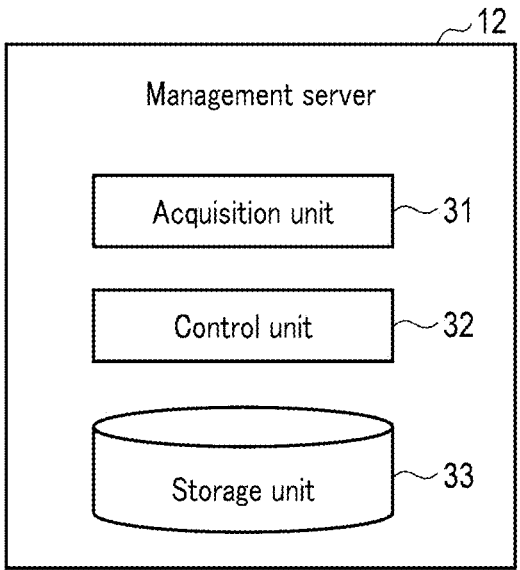
F I G. 8

MEDICATION USE SUPPORT SYSTEM

CROSS-REFERENCE TO RELATED APPLICATION

This application is a Continuation Application of PCT Application No. PCT/JP2023/026125, filed Jul. 14, 2023 and based upon and claiming the benefit of priority from Japanese Patent Application No. 2022-114191, filed Jul. 15, 2022, the entire contents of all of which are incorporated herein by reference.

FIELD

The present invention relates to a medication use support system that supports use of medicine.

BACKGROUND

Conventionally, there has been adopted a means for instructing the use of medicine prescribed from a medical institution or a dispensing pharmacy according to a medicine bag or an instruction sheet describing a medication use method so that a patient does not use an incorrect medicine.

In addition, for example, Jpn. Pat. Appln. KOKAI Publication No. 2003-16185 discloses a means for managing and notifying a patient's medication use status by using a wireless communication device in order to avoid a patient's forgetting to use medicine. Jpn. Pat. Appln. KOKAI Publication No. 2003-16185 discloses a medicine administration reminder notification system that collectively manages medicine administration information at a management center, and notifies a patient's mobile phone of a medication use time via wireless communication.

SUMMARY

According to one aspect of the present invention, a medication use support system is a medication use support system communication device provided to a medicine and a terminal that stores and manages medication information, wherein the terminal includes: a reading unit which reads first trigger information for acquiring information of the medicine; a communication unit which performs wireless communication with the communication device; a storage unit which stores management information of the medicine; a display unit which displays a medication use management screen including management information of the medicine; and a control unit which determines a use status of the medicine by communication with the communication device, the communication device is in an uncommunicable state with the terminal when shielded by an electromagnetic wave shielding member that shields an electromagnetic wave, and is in a communicable state with the terminal when not shielded by the electromagnetic wave shielding member, the communication device transmits second trigger information to the communication unit in the communicable state, and the control unit displays management information of the medicine stored in the storage unit on the display unit when the first trigger information is acquired, determines a use status of the medicine when the second trigger information is acquired, and displays the use status of the medicine to the management information of the medicine displayed on the display unit.

BRIEF DESCRIPTION OF THE DRAWINGS

FIG. 1 is an explanatory diagram illustrating a configuration of a medication use support system according to an embodiment of the present invention.

FIG. 2 is an explanatory diagram illustrating a configuration of the medication use support system.

FIG. 3 is a plan view illustrating a configuration of a patch and a communication device used in the medication use support system.

FIG. 4 is a cross-sectional view illustrating the configuration of the patch and the communication device.

FIG. 5 is a plan view illustrating a state in which the patch and the communication device are placed in a package.

FIG. 6 is an explanatory view illustrating a state in which the package is opened.

FIG. 7 is an explanatory view illustrating an example of use of a protective film used in the patch.

FIG. 8 is a block diagram illustrating a configuration of a management server used in the medication use support system.

DETAILED DESCRIPTION

Figure 9:
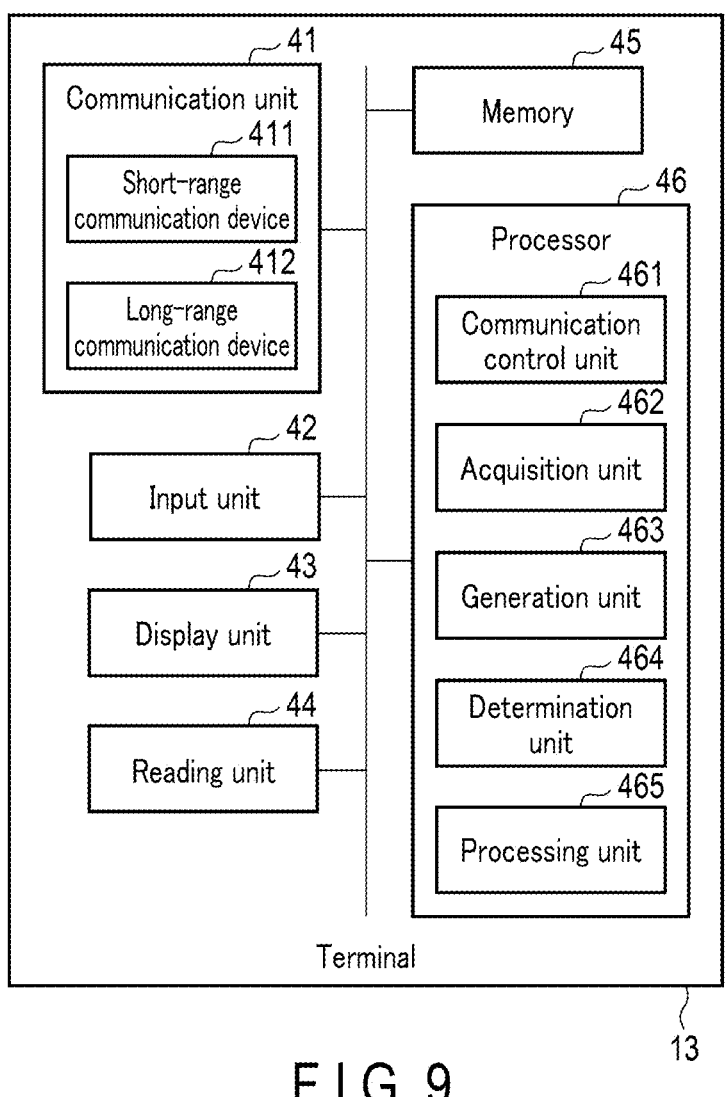
FIG. 9 is a block diagram illustrating a configuration of a terminal used in the medication use support system.
Figure 10:
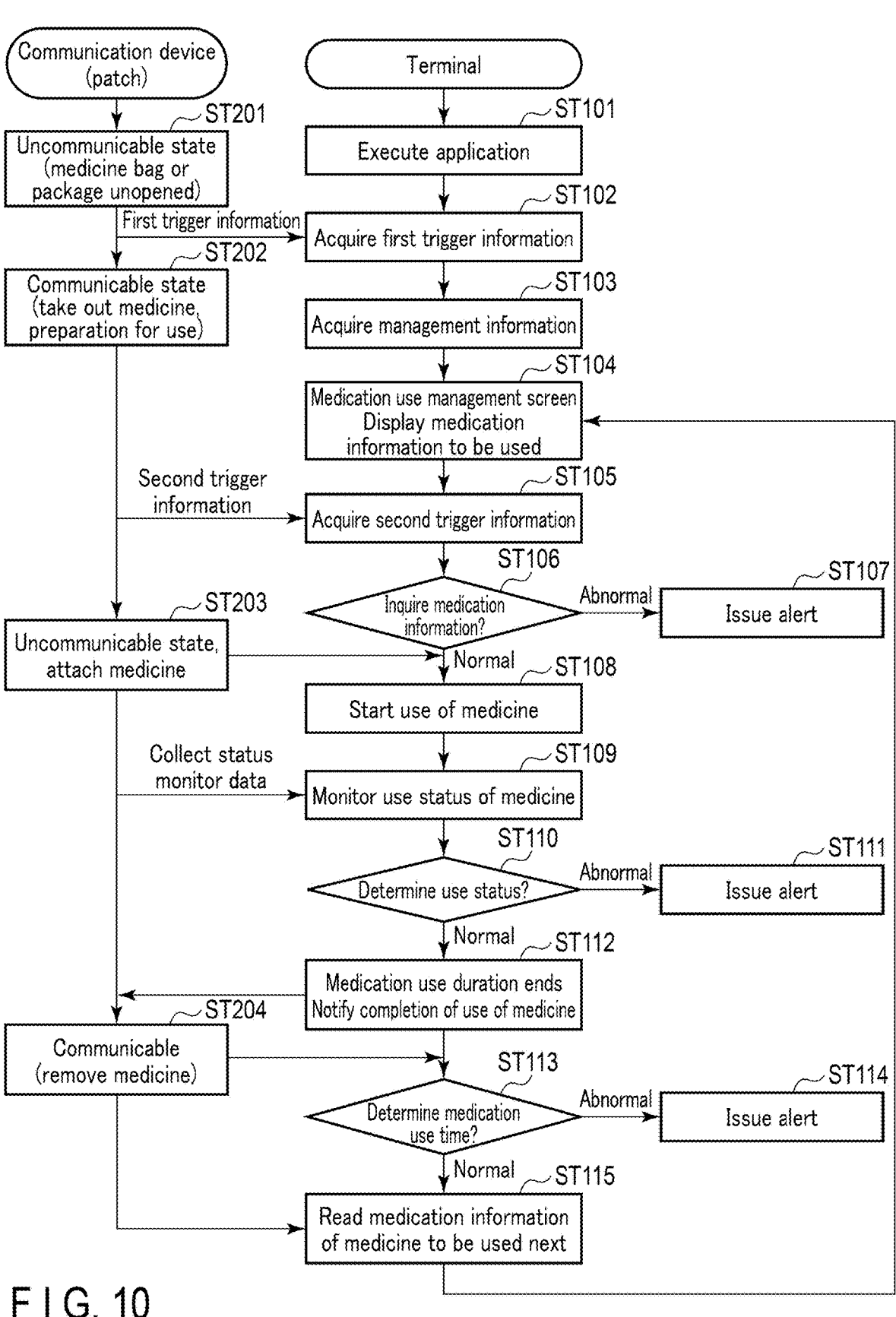
FIG. 10 is a sequence diagram of the communication device and the terminal of the medication use support system.

FIG. 1 is an explanatory diagram illustrating a configuration of a medication use support system 1 according to an embodiment of the present invention, and FIG. 2 is an explanatory diagram illustrating an example of use of the medication use support system 1. FIG. 3 is a plan view illustrating the configurations of a patch 10 and a communication device 11 used in the medication use support system 1, and FIG. 4 is a cross-sectional view illustrating the configurations of the patch 10 and the communication device 11. FIG. 5 is a plan view illustrating a state in which the patch 10 and the communication device 11 are placed in a package 25, and FIG. 6 is an explanatory view illustrating a state in which the package 25 is opened. FIG. 7 is an explanatory view illustrating an example of a protective film 23 used for the patch 10. FIG. 8 is a block diagram illustrating a configuration of a management server 12 used in the medication use support system 1, and FIG. 9 is a block diagram illustrating a configuration of a terminal 13 used in the medication use support system 1. FIG. 10 is a sequence diagram of the communication device 11 and the terminal 13 of the medication use support system 1.

As illustrated in FIG. 1 and FIG. 2, the medication use support system 1 includes the communication device 11 used for medicine 10, the management server 12, and the terminal 13. As illustrated in FIG. 2, the medication use support system 1 allows the terminal 13 to read a code 28, for example, a QR code (registered trademark), as first trigger information, stores the administration method of the medicine 10 defined by a medical institution in the terminal 13, and further uses this as a trigger to acquire management information of the medicine 10, such as a type, description, image, or the like of the medicine 10 from the management server 12 and to store the acquired management information in the terminal 13. In addition, the medication use support system 1 is a system that acquires second trigger information from the communication device 11, acquires and/or determines use status of the medicine 10 by the terminal 13 based on the acquired various types of information, and manages the use of medicine by a user (patient). In addition, for example, in a case where the terminal 13 acquires the second trigger information, the medication use support system 1 displays a screen of an application that manages the medication use support on the terminal 13 based on the stored management information, displays the management information of the medicine 10 on the screen of the application, and provides the management information of the medicine 10 to the patient to allows the patient to visually recognize the management information. In addition, the medication use support system 1 determines the use status of the medicine 10 of the patient by the terminal 13 based on the use status acquired from the communication device 11 through communication with the communication device 11, a QR code 28, and the management information acquired from the management server 12, and in a case where erroneous use is determined, the medication use support system 1 issues an alert to the patient by the terminal 13.

As illustrated in FIG. 1, in the medication use support system 1, each component transmits and receives information by communication means. As a specific example, it is assumed that the communication device 11 and the terminal 13 are connected by a relatively short-distance wireless communication means such as Bluetooth (registered trademark). Furthermore, as a specific example, the management server 12 and the terminal 13 are connected via a mobile communication network such as 4G or 5G or a wireless communication line of a relatively long distance such as Wimax via a network NW. Note that the management server 12 and the terminal 13 may be connected via a wired communication line such as an USB (universal serial bus) or a LAN (local area network) connection by a cable. Furthermore, the communication means is not limited thereto, and the communication device 11, the management server 12, and the terminal 13 may be connected by the other communication means than the above-described communication means.

The medicine 10 is used for various diseases. As illustrated in FIG. 3 and FIG. 4, the medicine 10 is, for example, a patch to be attached to a human body. Hereinafter, the medicine 10 will be described as a patch 10. The patch 10 is used, for example, in the treatment of bronchial asthma, ischemic heart disease, hypertension, overactive bladder, Alzheimer's disease, Parkinson's disease, attention deficit/hyperactivity disorder, schizophrenia, depression, postmenopausal osteoporosis, nausea, allergy, analgesia, smoking cessation, infertility, and the like. The patch 10 supplies the medicine into the body of the patient by transdermal absorption. The type, time, number, and the like of use of the patch 10 are determined.

For example, as illustrated in FIG. 5, when the patch 10 is packaged in the package 25 and prescribed by a pharmacy, a predetermined number of the patches 10 packaged in the packages 25 are placed in a medicine bag 26 for management together with an instruction sheet 27, as illustrated in FIG. 2. As shown in FIG. 6, the patch 10 is used, at the time of use, in a state where the package 25 is opened and the patch 10 is taken out from the package 25.

As a specific example, as shown in FIG. 3 and FIG. 4, the patch 10 includes a support body 21 having a sheet-like shape, a plaster 22 provided on one main surface of the support body 21, and a protective film 23 that protects the surface of the plaster 22. In addition, the patch 10 is, for example, placed in the package 25 and sealed.

The plaster 22 is provided on one main surface of the support body 21. In addition, the communication device 11 is provided on another main surface of the support body 21. That is, in the patch 10, the communication device 11 is provided on the surface of the support body 21 opposite to the surface provided with the plaster 22 that comes into contact with the patient's skin. The support body 21 is, for example, formed of a material having adhesiveness, or an adhesive layer having adhesiveness is formed on the surface on which the communication device 11 is provided, and the communication device 11 is detachably attached to the support body 21. For example, the support body 21 to which the communication device 11 is detachably attached may be provided with an adhesive on the surface on which the communication device 11 is provided, or the entire support body 21 may be formed of a material having adhesiveness. Note that the support body 21 may be formed of a sheet formed of a resin material, the communication device 11 may be fixed by a double-sided tape, an adhesive, or the like to the support body 21, and the communication device 11 may not be detachably attached, or may be difficult to be detachably attached.

The plaster 22 is formed of a medicine and an adhesive. The plaster 22 is configured such that the contained medicine can be percutaneously absorbed by contacting the skin.

The protective film 23 protects the plaster 22 by covering the plaster 22 before the plaster 22 is attached to the skin of the patient. When the plaster 22 is attached to the skin of the patient, the protective film 23 is peeled off from the plaster 22 as shown in FIG. 7. The package 25 packages and seals one or more patches 10.

At least one of the protective film 23 and the package 25 is an electromagnetic wave shielding member formed of a material having a function of shielding an electromagnetic wave. For example, the protective film 23 has a shielding property of shielding an electromagnetic wave. While the protective film 23 protects the plaster 22, the protective film 23 shields the electromagnetic wave from the communication device 11 provided on the support body 21 or allows the communication device 11 to be in an uncommunicable state. The package 25 has, for example, a shielding property of shielding an electromagnetic wave. While the patch 10 is packaged by the package 25, the package 25 shields the electromagnetic wave from the communication device 11 provided on the support body 21 or allows the communication device 11 to be in an uncommunicable state. For example, while the protective film 23 is attached to the plaster 22, the communication device 11 is brought into an uncommunicable state, and when the protective film 23 is peeled off from the plaster 22, the communication device 11 is activated and the communication device 11 is brought into a communicable state.

As illustrated in FIG. 2, the medicine bag 26 is a bag which indicates information such as a name of a patient, usage, dosage, a dispensing date, a name of a pharmacist who dispenses a medicine, a name and a location of a pharmacy, a hospital, a clinic or the like that has dispensed a medicine. As illustrated in FIG. 2, the instruction sheet 27 is a material for patients which indicates medication information such as a name of a medicine, efficacy, usage, dosage, and treatment schedule.

In addition, the code 28 associating information with the patch 10 is provided by being printed or being attached as a seal on which the code 28 is printed to at least any of the patch 10, the communication device 11 provided on the patch 10, the package 25 packaging the patch 10, the medicine bag 26, and the instruction sheet 27.

The code 28 is, for example, a one-dimensional code or a two-dimensional code, and is a QR code as a specific example. Hereinafter, the code 28 will be described as the QR code 28. The QR code 28 is first trigger information for acquiring information on the patch 10 to be managed in the terminal 13. The QR code 28 is coded information of the patch 10. Here, the information on the patch 10 can be, for example, information on the patch 10 itself, information on an administration method or the like determined in advance for the patch 10, or information on the use of a medicine for each patient by a doctor or a pharmacist, such as a method of using the patch 10 according to the patient (usage, dosage, treatment schedule). Note that the first trigger information only needs to be associated with the information acquired by the terminal 13 from the management server 12, and thus may be patient information instead of the information of the patch 10. That is, the first trigger information may include other information in addition to the information of the patch 10, or may be the information of the patch 10 itself.

The communication device 11 performs wireless communication with the terminal 13. The radio wave system of the communication device 11 is general, and any frequency band of 433 MHZ, 900 MHz band, or 2.45 GHz may be used regardless of the format as long as the terminal 13 can read the recorded information. The wireless communication technology used for the communication device 11 is, for example, Bluetooth (registered trademark) or Bluetooth Low Energy (BLE) (registered trademark). The communication device 11 may be, for example, an active tag or a passive tag.

In a case where the communication device 11 is an active tag, the communication device 11 may have a configuration including a battery, a power supply circuit, and the like, or may be a tag that performs energy harvesting. Preferably, the communication device 11 performs energy harvesting and is a battery-less tag. That is, the communication device 11 is a radio tag that operates by obtaining energy from surrounding electromagnetic waves. For example, examples of an energy harvesting type radio tag include an IoT sensing label "Wiliot IoT pixel" (manufactured by Wiliot). The communication device 11 may also be a type in which a temperature sensor is built.

As a specific example, the communication device 11 includes, for example, a tag antenna 11*a* including a matching circuit and an IC chip 11*b*. Furthermore, the communication device 11 includes a temperature sensor 11*c*. The IC chip 11*b* stores unique tag identification information, and transmits the unique tag identification information at the time of communication with the terminal 13. The temperature sensor 11*c* is built in the IC chip 11*b*, for example. The communication device 11 may be an RFID tag that communicates with the terminal 13 via a reader-writer.

The communication device 11 is fixed to the support body 21 of the patch 10, for example, and is packaged in the package 25 together with the patch 10. The communication device 11 may be attached by a patient to the support body 21 of the patch 10 taken out from the package 25.

When the patch 10 is applied to the skin of the patient, and when the plaster 22 is protected by the protective film 23 and/or packaged in the package 25, the communication device 11 is shielded from the electromagnetic wave and is to be uncommunicable. When the communication device 11 is taken out from the package 25, or the protective film 23 is peeled off before being attached to the skin, the shielding of the electromagnetic wave is released and is to be communicable. The communication device 11 transmits the second trigger information to the terminal 13 by communicating with the terminal 13. In addition to the second trigger information, the communication device 11 may transmit information of the patch 10 on which the communication device 11 is provided to the terminal 13.

The management server 12 is an example of a management device, and is a computer including a processor such as a CPU (Central Processing Unit), a memory such as a ROM (Read Only Memory) and a RAM (Random Access Memory), a display device, an input device, and a communication device. The management server 12 includes a mass storage device such as an HDD (Hard Disk Drive), an SSD (Solid State Drive), and an integrated circuit storage device for managing various data related to the plurality of patches 10. The mass storage device will be referred to as a database. For example, the management server 12 stores various data related to the patch 10 in a database, and manages the use status of the patch 10. Note that the management server 12 is not limited to an on-premises server, and may be a cloud server.

As a specific example, as illustrated in FIG. 8, the management server 12 includes an acquisition unit 31, a control unit 32, and a storage unit 33. The acquisition unit 31 and the control unit 32 are realized by, for example, a processor, and the storage unit 33 is realized by, for example, a memory and a mass storage device.

The acquisition unit 31 acquires use status of the patch 10 from the terminal 13. The use status of the patch 10 is, for example, communication information of the communication device 11 and the terminal 13, a time or a period such as an interval between communication and non-communication between the communication device 11 and the terminal 13, a communication date and time, or the like, and/or information transmitted from the communication device 11 and information regarding use of the patch 10 of the patient acquired or determined by the terminal 13 based on the information, or the like. In addition, the acquisition unit 31 acquires information input to the terminal 13 regarding use of the patch 10.

For example, the control unit 32 performs communication control for communicating information of the patch 10 or the like relative to the terminal 13. The storage unit 33 stores and manages information of the patch 10 used by a patient to be transmitted to the terminal 13, an application program (also referred to as an app or an application), update data, and the like used for medication use support in the terminal 13. Here, the information of the patch 10 is, for example, management information for medication use support. The management information is information for using the patch 10 such as information of the patch 10, a usage description of a method of using the patch 10, or the like and an attachment time (duration) and the number of times of attachment of the patch as an administration method. For example, the management information is general information of the patch 10 acquired from a pharmaceutical company or a company or a hospital to which information is provided from the pharmaceutical company. Furthermore, the information of the patch 10 includes, for example, medication information of the instruction sheet 27 such as the name, function, efficacy, use, and the like of the patch 10 used by the patient, and information that does not change depending on the patient, such as image data of the patch 10.

The terminal 13 is a communication terminal used by a patient who receives support (management) from the terminal 13 when the patient uses a medicine (uses the patch 10). Note that the terminal 13 is not necessarily used by the patient, and for example, the terminal 13 may be a communication terminal used by a family member of the patient, an assistant, or a medical person. The terminal 13 is, for example, a portable terminal that can be carried. Examples of the terminal 13 include a mobile terminal such as a smartphone, a feature phone, and a tablet, a wearable device such as a smart watch, and a notebook PC. Note that the terminal 13 may be a communication device exclusively configured to support (manage) medication use. For example, an application program dedicated to support medication use is installed in the terminal 13. Note that the terminal 13 may be configured to access, for example, a web browser dedicated to support medication use.

Here, the application is used to support (manage) medication use, but may have a function other than management. For example, the application dedicated to support medication use may have, for example, a function of obtaining medication information of the instruction sheet 27 or information regarding medication use that cannot be coded in the QR code 28 or the like, by issuing an instruction to a patient to manually input information, or a function of registering information such as a medication photograph or a detailed description of a medicine that cannot be coded in the QR code 28 or the like in the application program in advance and reading the information together with the medication use information. Furthermore, in a case where the management server 12 and the terminal 13 communicate with each other, the application may have a function of updating information such as a picture or detailed description regarding the medicine of the medication use application to new information at any time.

As a specific example, as illustrated in FIG. 9, the terminal 13 includes a communication unit 41, an input unit 42, a display unit 43, a reading unit 44, a memory (storage unit) 45, and a processor (control unit) 46.

The communication unit 41 communicates with the communication device 11 and the management server 12. The communication unit 41 includes, for example, a short-range communication device 411 and a long-range communication device 412.

The short-range communication device 411 is equipped with a wireless communication module conforming to a wireless communication standard such as Bluetooth and performs short-range wireless communication. The short-range communication device 411 transmits and receives various data to and from the communication device 11, and receives the use status of the patch 10 provided with the communication device 11.

The long-range communication device 412 performs long-range communication using wireless communication standards such as a mobile communication network, Wimax, Wi-Fi, or the like. The long-range communication device 412 transmits and receives various data to and from the management server 12 via a long-range communication line (network NW).

The input unit 42 is an input device that converts a patient's instruction into an electric signal. The input unit 42 is an input I/F for receiving a user input, and may be built in the terminal 13 or externally attached to the terminal 13. The input unit 42 is, for example, an operation panel, a touch panel, a keyboard, a mouse, various switches, or the like. Note that the input unit 42 may be a voice input device. The electric signal from the input unit 42 is supplied to the processor 46 via the bus.

The display unit 43 is an example of an output I/F for outputting an image according to the processing of the processor 46, and may include a display device for displaying a moving image, a still image, text, and the like. The display unit 43 may include a speaker for outputting sound, music, and the like, and a vibrator for outputting information by vibration. Therefore, the "display unit" may be read as an "output unit". The display unit 43 is, for example, a liquid crystal display, an organic electroluminescence (EL) display, a cathode ray tube (CRT) display, an LED display, or the like. The display unit 43 displays display data of the patch 10. The display unit 43 is an example of a display unit.

The reading unit 44 is a reader that reads the QR code 28 which is the first trigger information, and is, for example, a scanner or an imaging device. For example, in a case where the terminal 13 is a smartphone, the reading unit 44 is a camera as an imaging device mounted on the smartphone. In a case where the QR code 28 is within the reading range, the reading unit 44 reads information of the QR code 28 as first trigger information.

The memory 45 is a storage device such as an EEPROM (Electrically Erasable Programmable Read-Only Memory) (registered trademark), a ROM, a RAM, an HDD, an SSD, an integrated circuit storage device, or the like that stores various data. The memory 45 may be physically realized by one memory device or may be realized by a plurality of physically separated memory devices.

The memory 45 stores a program executed by the processor 46 in order for the processor 46 to realize each processing, an application program, data used by the processor 46, and the like. The memory 45 may include RAM having a work area in which such programs/data are deployed. As the program, for example, firmware, an OS, a communication program, and the like are appropriately stored. The application program is, for example, application software that operates for supporting (managing) medication use on the OS. In addition, the memory 45 constructs a database, stores information such as a unique ID of the communication device 11 and information of the patch 10 received from the management server 12, and stores various types of information such as a communication state, a communication start time, a communication interruption time, the number of communications, and communicated information relative to the communication device 11.

The processor 46 is an arithmetic device such as a CPU or a microprocessor. Note that the processor 46 may be an FPGA, a DSP, a GPU, an ASIC, another general-purpose or dedicated processor, or the like. The processor 46 executes various programs stored in the memory 45 to execute a function (processing) as support for medication use and a function (processing) of communicating with the communication device 11 and the management server 12 via the communication unit 41 and managing information acquired from the communication device 11 and the management server 12. The processor 46 executes the program and/or the application program stored in the memory 45 to realize each function of a communication control unit 461, an acquisition unit 462, a generation unit 463, a determination unit 464, and a processing unit 465. Note that the function division for each unit in the processor 46 is described for convenience and can be changed as appropriate. Furthermore, the communication control unit 461, the acquisition unit 462, the generation unit 463, the determination unit 464, and the processing unit 465 are assumed to be carried out by one processor 46, but may be shared by a plurality of physically separated processors.

The communication control unit 461 transmits and receives information relative to the communication device 11 to which connection is established via the short-range communication device 411. In addition, the communication control unit 461 transmits and receives information of the patch 10 relative to the management server 12 via the long-range communication device 412.

For establishing a wireless connection, for example, a wireless connection may be established by a general pairing connection for Bluetooth, and a wireless connection may be established by inputting an SSID and a password set in advance to an access point of Wi-Fi for Wi-Fi.

For example, the communication control unit 461 controls the short-range communication device 411 to communicate with the communication device 11. For example, the communication control unit 461 transmits a connection request to the communication device 11 that has transmitted an advertisement packet. Furthermore, the communication control unit 461 may transmit some data for establishing a connection with the communication device 11 via the short-range communication device 411, or may transmit a request to the communication device 11 in response to an operation of the patient. Alternatively, the communication control unit 461 may receive some data for establishing a connection with the communication device 11, for example, information of the communication device 11 from the management server 12 in advance, and transmit a request to the communication device 11. Furthermore, after transmitting the connection request to the communication device 11, the communication control unit 461 performs GATT communication with the communication device 11. For example, once the wireless connection with the communication device 11 is established, the communication control unit 461 automatically establishes the wireless connection with the communication device 11 from the next time.

The acquisition unit 462 acquires first trigger information that is information of the patch 10 as medication information or patient information from the QR code 28 read by the reading unit 44. The information of the patch 10 is, for example, information for using the patch 10 such as an attachment time (duration) and the number of times of attachment of the patch as an administration method. The acquisition unit 462 acquires management information for medication use support received from the management server 12 based on the first trigger information. Examples of the management information include information of the patch 10, a method of using the patch 10, and the like. The information of the patch 10 includes the name, function, efficacy, use, image data, and the like of the patch 10. In addition, the management information is not limited thereto, and appropriately includes information used for medication use support. In addition, the acquisition unit 462 acquires second trigger information from the communication device 11 and acquires the communication status with the communication device 11. Here, the communication status with the communication device 11 is, for example, information and a duration of disconnection of communication with the communication device 11 after acquisition of the second trigger information, information and a duration of communication after disconnection of communication with the communication device 11, and the like. The acquisition unit 462 stores the acquired information in the memory 45.

The generation unit 463 generates a management pattern of the patch 10 to be applied to the patient based on the management information acquired by the acquisition unit 462. The management pattern is, for example, a time for attaching the patch 10 (medication use set duration), a time zone, a duration, the number of times, and the like. In addition, in a case where different patches 10 are applied, in a case where a plurality of patches 10 are attached for different durations, or the like, the order of attachment of the different patches 10, the time schedule, and the like can be included. In addition, the generation unit 463 generates a display pattern of a medication use management screen to be displayed on the display unit 43 when the application is executed based on the management information acquired by the acquisition unit 462 and the generated management pattern. Here, as in an example illustrated in FIG. 2, the display pattern (medication use management screen)

includes information of the patch 10, a method of using the patch 10, propriety of preparation of management (support), propriety of a type of a medication to be used, a treatment status, a duration (time) for attaching the patch 10, the number of times of attaching the patch 10, quality of the use status of the patch 10, and the like.

As the information of the patch 10, for example, the instruction sheet 27 includes medication information such as a name, efficacy, usage, and dosage of a medicine. The treatment status includes, for example, forgetting to use the patch 10. The duration (time) in which the patch 10 is attached includes, for example, a medication use duration which is a duration in which the patient has attached the patch 10 and a duration in which the patient attaches the patch 10. The number of times of attaching the patch 10 includes, for example, the number of times of using a medicine which is the number of times that the patient has used the patch 10, and the number of times that the patient uses the patch 10. The quality of the use status of the patch 10 includes, for example, a result of determining the status of the patch 10 actually applied to the patient.

The determination unit 464 determines the use status of the patch 10 used by the patient from the communication status of the communication device 11, and determines whether the type and method of using of the patch 10 which are the management information are different from the use status of the patch 10 used by the patient. For example, the determination unit 464 determines propriety of preparation of management, propriety of a type of the patch 10 (medicine) to be used, a treatment status, a duration for attaching the patch 10, the number of times of attaching the patch 10, a status of attachment of the patch 10, based on the communication status with the communication device 11 acquired by the acquisition unit 462 and the management information.

The "propriety of preparation for management" is, for example, whether or not preparation for starting a support processing for medication use using the terminal 13 is completed. As the propriety of preparation for management, the determination unit 464 determines, for example, whether or not the communication device 11 provided to the patch 10 is communicable and has acquired the second trigger information. In a case where the acquisition unit 462 has acquired the second trigger information, the determination unit 464 determines that the patient is in a state where the patient's act of using the medicine 10, that is, the preparation for management is completed, and management can be started. In a case where the acquisition unit 462 has not acquired the second trigger information, the determination unit 464 determines that the preparation for management is not completed.

The "propriety of a type of the patch 10 (medicine) to be used" is, for example, whether or not the patch 10 to be applied to the patient defined in the management information and the patch 10 for which the package 25 is opened and prepared to use by the patient match each other.

As propriety of a type of the patch 10 (medicine) to be used, for example, the determination unit 464 compares the information of the patch 10 transmitted from the communication device 11 acquired together with the second trigger information in the acquisition unit 462 with the information of the patch 10 acquired from the QR code 28, and determines whether or not the type of the patch 10 to be used appropriate. In the determination, the determination unit 464 may use the information of the patch 10 acquired from the management server 12 in addition to the information of the patch 10 acquired from the QR code 28, or the determination unit 464 may use the information of the patch 10 acquired from the management server 12 instead of the information of the patch 10 acquired from the QR code 28. In a case where the information from the communication device 11 matches the information acquired from the QR code 28 and/or the management server 12 for the patch 10, the determination unit 464 performs a consistency determination (correct determination) of the type of the patch 10 to be used, and in a case where the information from the communication device 11 does not match the information acquired from the QR code 28 and/or the management server 12 for the patch 10, the determination unit 464 performs an inconsistency determination (failure determination) of the type of the patch 10 to be used.

Alternatively, as the propriety of the type of the patch 10 (medicine) to be used, the determination unit 464, for example, determines the propriety of the type of the patch 10 by, the patient comparing (inquiring) the patch 10 displayed on the display unit 43 with the patch 10 at hand and inputting that the type of the patch 10 matches using the input unit 42.

The "treatment status" is, for example, a use status of the patch 10. As the treatment status, the determination unit 464 determines, for example, before use of the patch 10, start of use (in use) of the patch 10, and completion of use of the patch. For example, the determination unit 464 acquires the second trigger information, and determines that it is before use of the patch 10 in a case where communication with the communication device 11 is continued. For example, in a case where communication with the communication device 11 is disabled after acquiring the second trigger information, the determination unit 464 determines that the patch 10 is started to be used (in use). In addition, for example, the determination unit 464 determines that a duration during which communication with the communication device 11 is continuously disabled after determining the status as the start of use of the patch 10 is the medication use duration, and the determination unit 464 determines that the use of the patch 10 is completed in a case where communication with the communication device 11 is disabled after acquiring the second trigger information, and the communication device 11 is communicated again.

The "duration for attaching the patch 10" is, for example, the time elapsed from the start of use of the patch 10 and/or the remaining use time of the patch 10. As the duration for attaching the patch 10, for example, the determination unit 464 counts the elapsed time from the time when the start of use of the patch 10 is determined, or stores the time when the start of use is determined, and calculates the elapsed time from the current time to determine the duration (time) in which the patch 10 is attached.

In addition, the determination unit 464 determines the remaining time to attach the patch 10 by subtracting the duration (time) in which the patch 10 is attached from the acquired time for attaching the patch 10 to be used (medication use set duration). In addition, the determination unit 464 determines that the time for attaching the patch 10 (medication use set duration) has elapsed (the remaining time for attaching the patch 10 has become 0).

The "number of times of attaching the patch 10" is, for example, the number of attached patches 10 and/or the remaining number of patches 10 scheduled to be attached among a predetermined number of patches 10 scheduled to be attached defined in the management information. As the number of times of attaching the patch 10, for example, the determination unit 464 determines the number of times of determining that the use of the patch 10 has been completed after the time for attaching the patch 10 (medication use set duration) has elapsed. In addition, the determination unit

464 subtracts the number of times of attaching the patch 10 from the number of times of using the patch 10 acquired from the management server 12, and determines the remaining number of times of attaching the patch 10.

The "status of attachment of the patch 10" is, for example, a use status of the patch 10 attached to the skin after the start of use of the patch 10, and indicates, for example, whether or not the patch 10 is normally attached and whether or not the patch 10 is attached for a predetermined use time. As the status of attachment of the patch 10, the determination unit 464 determines, for example, a state in which the patch 10 is attached, that is, a state in which the patch 10 is not attached well or is peeled off. As a specific example, the determination unit 464 determines that the status of attachment of the patch 10 is defective in a case where a communicable state and an uncommunicable state with the communication device 11 repeatedly occur after determining that the patch 10 is started to be used, or in a case where communication with the communication device 11 is performed before the elapse of the duration of attaching the patch 10. In addition, the determination unit 464 determines that the status of attachment of the patch 10 is good in a case where the state of uncommunicable with the communication device 11 continues after determining that the patch 10 is started to be used and before the elapse of the duration of attaching the patch 10.

In addition, as the status of attachment of the patch 10, the determination unit 464 determines whether or not the medicine has been removed after determining that the time for attaching the patch 10 (medication use set duration) has elapsed (the remaining time for attaching the patch 10 has become 0), and before a predetermined time has elapsed. As a specific example, the determination unit 464 determines whether or not it is determined that the use of the patch 10 is completed after the time for attaching the patch 10 (medication use set duration) has elapsed, and before the time stored in the memory 45 in advance elapses.

In a case where it is determined that the use of the patch 10 is completed after the time for attaching the patch 10 (medication use set duration) has elapsed, and before the time stored in the memory 45 in advance elapses, the determination unit 464 determines that the normal removal has been performed and the use time is normal. In addition, in a case where it is not determined that the use of the patch 10 is completed even after the time for attaching the patch 10 (medication use set duration) has elapsed, and the time stored in the memory 45 in advance has elapsed, the determination unit 464 determines that the use time of the patch 10 is abnormal in which the removal of the patch 10 is not performed, and the use time of the patch 10 is longer than the predetermined time.

Note that the determination unit 464 transmits the determined information to the generation unit 463 and the processing unit 465, the generation unit 463 reflects the information in a display pattern for generating the information and displays the information on the display unit 43, and the processing unit 465 stores the determined information in the memory 45. As a result, the patient can confirm, based on the display unit 43, the propriety of preparation of management, the propriety of a type of the patch 10 (medicine) to be used, the treatment status, the duration for attaching the patch 10, the number of times of attaching the patch 10, the status of attachment of the patch 10, and the like.

The processing unit 465 executes information processing such as an input command from the input unit 42, a unique ID acquired from the management server 12 and/or the communication device 11, information of the patch 10, execution of an application for medication use support, management of information such as a communication state, a communication start time, a communication interruption time, and the number of communications, parameter browsing/changing, program updating, and the like.

For example, when a command to execute an application is input from the input unit 42, the processing unit 465 executes the application. In addition, in a case where the QR code 28 is read by the reading unit 44 and the first trigger information is acquired as the function of the application, the processing unit 465 communicates with the management server 12, receives various types of information from the management server 12, and stores the information in the memory 45. From the various types of information, the generation unit 463 displays a part of the received content on the medication use management screen of the application displayed on the display unit 43. The processing unit 465 performs processing of obtaining a communication time from the time when communication with the communication device 11 is started and the time when communication is blocked.

For example, in a case where the determination unit 464 determines that the time for attaching the patch 10 (medication use set duration) has elapsed (the remaining time for attaching the patch 10 has become 0), the processing unit 465 displays a command to the patient for removing the patch 10 on the medication use management screen of the display unit 43.

The processing unit 465 issues an alert in a case where the wrong patch 10 is used, for example, in a case where the information determined by the determination unit 464 is determined as abnormal. As the alert activation, the processing unit 465 causes the display unit 43 to display information notifying abnormality. Note that the processing unit 465 may issue an alert by sound from a speaker and/or vibration from a vibrator in addition to the display on the display unit 43 or instead of the display on the display unit 43.

Examples of the abnormality determination include the inconsistency determination of the type of the patch 10 to be used, the defect determination of the status of attachment of the patch 10, and the use time abnormality determination of the patch 10 by the determination unit 464, but are not limited thereto.

In addition, the processing unit 465 stores the information determined by the determination unit 464 in the memory 45 in association with the determined time, and controls the communication unit 41 to transmit the information to the management server 12.

Next, an example of a management processing using the medication use support system 1 configured as described above will be described with reference to a sequence diagram illustrated in FIG. 10. An example of an action performed by the patient will also be described in the flow of the management processing.

First, in a case where a patient uses the patch 10, the patient operates the input unit 42 to input an application start command. The processor 46, for example, by the processing unit 465, executes the application program from the input unit 42 (step ST101). At this time, for example, the patch 10 is packaged in the package 25 and placed in the medicine bag 26 in an unopened state, and the communication device 11 is in an uncommunicable state (step ST201).

After the app is activated, the patient operates the terminal 13 to allow the reading unit 44 to read the QR code 28 indicated on the medicine bag 26, the instruction sheet 27, or the like in order to acquire the first trigger information to receive the medication use support by the app. The processor 46 acquires, by the acquisition unit 462 and the processing unit 465, the first trigger information from the QR code 28 read at the reading unit 44 (step ST102). In a case where the first trigger information is acquired, the processor 46 controls, by the communication control unit 461, the long-range communication device 412, communicates, by the acquisition unit 462, with the communication device of the management server 12, and acquires management information for medication use support, which is information of the patch 10 stored in the storage unit 33 of the management server 12 (step ST103). The processor 46 stores, by the processing unit 465, the acquired management information in the memory 45. In addition, the processor 46 generates, by the generation unit 463, the medication use management screen to be displayed on the display unit 43 of the terminal 13, and displays the medication use management screen and information (management information) of the patch 10 to be used on the display unit 43 (step ST104).

When the medication use management screen is confirmed, the patient opens the package 25 as shown in FIG. 6, takes out the patch 10, and peels off the protective film 23 from the plaster 22 as shown in FIG. 7 as a preparation for use. As a result, the communication device 11 enters a communicable state (ST202). As a result, the communication device 11 and the terminal 13 perform communication, and the second trigger information is transmitted from the communication device 11. The processor 46 acquires the second trigger information by the communication control unit 461 and the acquisition unit 462 (ST105). When the second trigger information is acquired, the processor 46 determines, by the determination unit 464, that the preparation for management is completed and displays, by the processing unit 465, the completion of the preparation for management on the medication use management screen of the display unit 43.

The processor 46 inquires of the patch 10 by the determination unit 464 (step ST106). As a specific example, the processor 46 determines, by the determination unit 464, the propriety of the type of the patch 10 (medicine) to be used. In a case where the inconsistency determination is made for the type of the patch 10 to be used, the processor 46 determines that it is abnormal, and controls by the processing unit 465 the display unit 43 to issue an alert (step ST107).

In the case where the consistency determination (correct determination) is made for the type of the patch 10 to be used, the processor 46 determines that it is normal, and controls by the processing unit 465 the display unit 43 to display that the type of the patch 10 is normal on the medication use management screen of the display unit 43.

When the patient confirms that the type of the patch 10 is normal from the display on the display unit 43, the patient attaches the patch 10 to the skin. As a result, the communication device 11 enters an uncommunicable state (step ST203).

In a case where the communication unit 41 cannot communicate with the communication device 11, and the acquisition unit 462 cannot acquire information, the processor 46 determines that the use of the patch 10 has started (step ST108). The processor 46 monitors the use status of the patch 10 (step ST109).

As the monitoring of the use status of the patch 10, the processor 46 determines, for example, the remaining time for attaching the patch 10, and determines, by the determination unit 464, normality or abnormality of the use status of the patch 10, such as whether the patch 10 is not removed, the attachment state e of the patch 10 is not defective, or the like before the time for attaching the patch 10 (medication use set duration) elapses (step ST110). In a case where the communication device 11 and the communication unit 41 communicate with each other due to removal of the patch 10, a defective attachment state, or the like before the elapse of time for attaching the patch 10, and the second trigger information is acquired, the processor 46 issues an alert by the display unit 43 as determining that the use status is abnormal (step ST111).

In a case where the use status is normal and the remaining time for attaching the patch 10 becomes 0, the processor 46 determines, by the determination unit 464, the end of the use duration of the patch 10, determines that the use of the patch 10 is completed, and displays a notification of the completion of use of the patch 10 on the display unit 43 (step ST112).

When the patient confirms the notification of the completion of use of the patch 10 displayed on the display unit 43, the patient removes the patch 10 from the skin. As a result, the communication device 11 enters a communicable state (step ST204).

The processor 46 determines, by the determination unit 464, whether the medicine has been removed, that is, whether the medication use time is normal or abnormal before a predetermined time elapses after it is determined that the time for attaching the patch 10 (medication use set duration) has elapsed (step ST113). For example, in a case where the communication unit 41 cannot communicate with the communication device 11 even after the predetermined time has elapsed, the processor 46 determines that the patch 10 has not been removed even after the predetermined time has elapsed, and determines that the medication use time is abnormal. In a case where it is determined that the medication use time is abnormal, the processor 46 issues, by the display unit 43, an alert indicating the time from the start of use of the patch 10 (step ST114).

In a case where the communication unit 41 can communicate with the communication device 11 before the predetermined time elapses, the processor 46 determines that the patch 10 is removed and determines that the medication use time is normal. Then, information of the patch 10 to be used next is read from the management information stored in the memory 45 (step ST115), and the process returns to step ST104. Note that the processor 46 determines the number of times of determining the completion of use of the patch 10 before or after step ST115, and subtracts the number of times of attaching the patch 10 from the number of times of using the patch 10 acquired from the management server 12, and determines whether or not the remaining number of times of attaching the patch 10 becomes 0, that is, whether or not the treatment with all the patches 10 has been completed. The processor 46 displays information of the treatment completion on the display unit 43 in a case where the treatment has been completed.

The patient repeatedly uses the prescribed patch 10 based on the display on the display unit 43. When the patient confirms that the treatment with the patch 10 has been completed on the display unit 43, the patient issues a command to stop the application via the input unit 42, and terminates the medication use support.

According to the medication use support system 1 configured as described above, by displaying the management information of the patch 10 on the display unit 43 to the user as the medication use support by the terminal 13, the patient can confirm various types of information such as the status of use and the method of use of the medicine (patch) 10. As a result, the medication use support system 1 can prevent the patient from missing the timing of medication use and forgetting to use the medicine, and can manage to reliably use the medicine 10 according to the instruction of the method of using the medicine 10.

In addition, the terminal 13 displays a medication use management screen on the display unit 43, regarding management information such as a method of using including the type of the medicine 10 acquired (associated) based on the first trigger information acquired from the QR code 28 and/or the first trigger information acquired from the communication device 11, and the status of use of the medicine 10 used by the patient, and issues an alert. Thus, the patient can confirm the incorrect use of medicine 10, which is different from the method of using the medicine 10.

That is, even when there is a variation in the type and amount of the medicine 10 to be used, the timing of use, and the like, the medication use support system 1 can display appropriate information according to the time of use and the use situation. In addition, in the medication use support system 1, since the determination unit 464 can determine the erroneous use (abnormality) of the medicine 10 and issue an alert at the time of abnormality, it is possible to prevent the patient from mistakenly using a different medicine 10, or from mistakenly using the medicine 10 in an incorrect order of use, amount of use, and number of times of use. In addition, since the medication use support system 1 can determine the use status of the medicine 10 based on the actual medication use status of the patient, the medication use of the patient can be managed with high accuracy. In this manner, the medication use support system 1 can support the patient based on the medication use status.

In addition, the medication use support system 1 has a configuration using the protective film 23 and/or the package 25 or a configuration in which the patch 10 is attached to the skin to shield the electromagnetic wave, thereby making the communication device 11 in the uncommunicable state. In addition, the medication use support system 1 is configured to bring the communication device 11 into the communicable state by taking out the patch 10 from the package 25, peeling off the protective film 23, and peeling off the patch 10 from the skin in order to make the patch 10 to be usable, for example. Therefore, since the medication use support system 1 can switch the communication state of the communication device 11 by the act of the patient using the patch 10, it is not necessary for the patient to perform a complicated operation, and the medication use support system 1 has high usability and can reduce the burden on the patient.

As described above, according to the medication use support system 1 according to the embodiment of the present invention, support based on the medication use status can be performed.

Note that the present invention is not limited to the above-described embodiments. In the above-described example, the configuration in which a patch is used as an example of the medicine 10 has been described, but the present invention is not limited thereto. That is, the medicine 10 may be another medicine 10 as long as the communication device 11 can be provided.

In the example described above, the communication device 11 is in the uncommunicable state when the patch 10 is attached to the skin, but the present invention is not limited thereto. For example, the communication device 11 may be configured to be communicable even when the patch 10 is attached to the skin. In this case, the communication device 11 may be configured to determine that the patch 10 is started to be used in a case where the temperature sensor 11c which detects the temperature detects the body temperature of the patient, and determine a period in which the temperature sensor 11*c* detects the body temperature of the patient, for example, a period in which there is no change in the temperature information detected by the temperature sensor 11*c*, as the medication use duration.

In the example described above, the medication use support system 1 includes the communication device 11, the management server 12, and the terminal 13, but is not limited thereto. For example, the medication use support system 1 may further include a server provided in a medical institution, a pharmacy, or the like. For example, in such a configuration, the terminal 13 and/or the management server 12 can transmit the use status of the medicine 10 to the server, or the terminal 13 and/or the management server 12 can receive the latest information regarding the management information of the medicine 10 from the server and update the management information. As a result, it is possible to grasp the treatment progress of the patient in a medical institution or the like.

In addition, a medical institution, a pharmacy, or the like may store a method of using the medicine 10 (usage, dosage, treatment schedule, etc.) of each individual patient in a medical institution server, and the patient may read a code with the terminal and receive the treatment method according to the code from the medical institution server. Note that, as the code, various codes can be applied as long as the codes can be read by the terminal 13.

Furthermore, in the above-described example, an example has been described in which the processor 46 of the terminal 13 of the medication use support system 1 issues an alert in a case where the result of inquiring the medication information indicates a different medicine 10 in step ST106 (step ST107), but the present invention is not limited thereto. For example, in a case where an incorrect medicine 10 is opened, the input unit 42 of the terminal 13 may be configured to input a reset input, and in a case where the input unit 42 inputs the reset input, the process may return to step ST104. In such a case, the patient may refill the protective film 23 of the incorrect medicine 10, store it again in the package 25, seal it, open the correct medicine 10 from the package 25, and peel off the protective film 23.

That is, the present invention is not limited to the above embodiment, and various modifications can be made in the implementation stage without departing from the gist thereof. In addition, each embodiment may be implemented in a suitable combination with others. If this is the case, combined effects can be attained. Furthermore, the above embodiments include inventions at various stages, and various inventions can be extracted by an appropriate combination of a plurality of disclosed constitutional requirements. For example, even if some constituent elements are deleted from all the constituent elements shown in the embodiments, when the problem can be solved and the effect can be obtained, the configuration from which the constituent elements are deleted can be extracted as the invention.

The invention claimed is:

1. A medication use support system comprising a communication device provided to a medicine and a terminal that stores and manages medication information, wherein the terminal comprises:
   a reading unit configured to read first trigger information for acquiring information of the medicine;
   a communication unit configured to perform wireless communication with the communication device;
   a storage unit configured to store management information of the medicine;

a display unit configured to display a medication use management screen including the management information of the medicine; and
   a control unit configured to determine a use status of the medicine by communication with the communication device,
   the communication device is in an uncommunicable state with the terminal when shielded by an electromagnetic wave shielding member that shields an electromagnetic wave, and is in a communicable state with the terminal when not shielded by the electromagnetic wave shielding member, and the communication device transmits second trigger information to the communication unit in the communicable state, and
   the control unit displays management information of the medicine stored in the storage unit on the display unit in a case where the first trigger information is acquired, determines a use status of the medicine in a case where the second trigger information is acquired, and displays the use status of the medicine to the management information of the medicine displayed on the display unit.

2. The medication use support system according to claim 1, wherein
   the communication device is a radio tag that is provided to the medicine, stores unique tag identification information, and operates by obtaining energy from a surrounding electromagnetic wave, and
   the medicine is a patch in which the communication device is provided on a surface opposite to a surface in contact with a skin of a patient.

3. The medication use support system according to claim 2, wherein
   the communication device is in an uncommunicable state in a case where the medicine comes into contact with the skin, and
   the control unit becomes communicable in a case where the electromagnetic wave shielding member is removed, determines this state as an act of the patient using the medicine in a case where the second trigger information is acquired, determines that use of the medicine is started in a case where communication with the communication device is disabled after acquiring the second trigger information, and determines a duration during which an uncommunicable state with the communication device is continued after use of the medicine is started as a medication use duration.

4. The medication use support system according to claim 2, wherein
   the communication device includes a temperature sensor, and
   the control unit becomes communicable in a case where the electromagnetic wave shielding member is removed, determines this state as an act of the patient using the medicine in a case where the second trigger information is acquired, determines that use of the medicine is started in a case where the temperature sensor detects a body temperature of the patient after acquiring the second trigger information, and determines a duration during which the temperature sensor detects the body temperature as a medication use duration.

5. The medication use support system according to claim 1, wherein the medication use management screen includes the medication information of the medicine, a method of using the medicine, a medication use duration, a number of times of using medicine, forgetting to use medicine, a type of medicine, and a state in which the medicine is attached.

6. The medication use support system according to claim 5, wherein the control unit determines a use status of the medicine based on a communication status with the communication device, and issues an alert when determining that the use status is different from a method of using the medicine.

7. The medication use support system according to claim 1, wherein the control unit issues an alert when acquiring the second trigger information from the communication device before a medication use set duration of the medicine elapses.

8. The medication use support system according to claim 2, wherein the control unit issues an alert in a case of acquiring the second trigger information from the communication device before a medication use set duration of the medicine elapses.

9. The medication use support system according to claim 3, wherein the control unit issues an alert when acquiring the second trigger information from the communication device before a medication use set duration of the medicine elapses.

10. The medication use support system according to claim 4, wherein the control unit issues an alert when acquiring the second trigger information from the communication device before a medication use set duration of the medicine elapses.

11. The medication use support system according to claim 5, wherein the control unit issues an alert when acquiring the second trigger information from the communication device before a medication use set duration of the medicine elapses.

12. The medication use support system according to claim 6, wherein the control unit issues an alert when acquiring the second trigger information from the communication device before a medication use set duration of the medicine elapses.

* * * * *